(12) United States Patent
Wang et al.

(10) Patent No.: US 6,201,390 B1
(45) Date of Patent: Mar. 13, 2001

(54) DEFECT ANALYSIS IN MAGNETIC THIN FILMS

(75) Inventors: Jian-Ping Wang; Lea Peng Tan; Thomas Yun Fook Liew, all of Singapore (SG)

(73) Assignee: Data Storage Institute, Singapore (SG)

( * ) Notice: Subject to any disclaimer, the term of this patent is extended or adjusted under 35 U.S.C. 154(b) by 0 days.

(21) Appl. No.: 09/377,828

(22) Filed: Aug. 20, 1999

(30) Foreign Application Priority Data

Aug. 27, 1998 (SG) ........................................ 9803330

(51) Int. Cl.[7] ........................ G01R 33/12; G01N 27/72; G01N 27/82
(52) U.S. Cl. ............................ 324/210; 324/212; 324/238
(58) Field of Search ................................. 324/210, 228, 324/237, 238, 240, 212

(56) References Cited

U.S. PATENT DOCUMENTS

| | | | | |
|---|---|---|---|---|
| 4,843,316 | * | 6/1989 | Hesterman | 324/210 |
| 5,637,999 | * | 6/1997 | Hennecken | 324/212 |
| 5,901,001 | * | 5/1999 | Meyer et al. | 360/25 |
| 6,014,282 | * | 1/2000 | Ito | 360/75 |
| 6,019,503 | * | 2/2000 | Abraham et al. | 374/4 |

OTHER PUBLICATIONS

Brown, William F., "The Effect of Dislocations on Magnetization Near Saturation," Phys. Rev. 60, 139–147, Jun., 1941.*

Neel, Louis, "Approach to Saturation," Chapter V in "Selected Works of Louis Neel," Nicholas Kurti, Ed., pp. 161–176, Gordon and Breach Science Publishers, New York & London (1988).*

* cited by examiner

Primary Examiner—Christine Oda
Assistant Examiner—Henry A. Andersen
(74) Attorney, Agent, or Firm—Nixon & Vanderhye P.C.

(57) ABSTRACT

A method of analyzing defects in a magnetic thin film is provided. A magnetic field is applied to the magnetic thin film. The magnetization of the magnetic thin film is measured over a range of different field strengths. A value representative of a magnetic hardness coefficient is calculated for the magnetic thin film from the magnetizations measured. The calculated value is compared with a reference value. Defect information is determined in dependence upon the comparison made. The defect information determined may relate to: (a) the relative levels of defects, if the reference value is representative of the magnetic hardness coefficient of a control specimen having a predetermined defect level; (b) the predominant type of defects, if the reference value is representative of the magnetic hardness coefficient obtained when the magnetic field is applied in a different direction; and (c) the distribution of defects, if the magnetizations are measured for a selected part of the magnetic thin film and compared with a reference value which is representative of a magnetic hardness coefficient calculated from magnetizations measured for a part other than the selected part of the magnetic thin film.

14 Claims, 3 Drawing Sheets

Magnetic Hardness Coefficient vs. Bias Voltage for CoCrTaPt/Cr/CoCrTaPt thin film media

DEFECT ANALYSIS IN MAGNETIC THIN FILMS

FIELD OF INVENTION

The present invention relates to a method of analyzing defects in a magnetic thin film, for example to determine relative levels of defects, the predominant type of defects, or defect distribution; and particularly, but not exclusively, to analyzing nano-sized defects in a magnetic thin film.

BACKGROUND OF INVENTION

Defects in magnetic thin films occur at the surface or within the film (in-depth). As the size of modern magnetic devices (such as magnetic read and write heads, recording thin film media and other magnetic sensors) is reduced, the thickness of magnetic thin films is also reduced. Indeed, the thickness of some of the magnetic thin films is approaching the nanoscale range. With increased miniaturization, the influence of nanoscale defects such as voids or dislocations in the magnetic thin films cannot be neglected. Taking the magnetic recording hard disk thin film media as an example, it is known that one of the most important reasons for high error rate of hard disk drives is due to contamination and defects on and in the thin film media. Furthermore, as the thickness of the magnetic layer for the hard disk thin film media decreases to around 10 nm and the average size of magnetic grains decreases to around 7.5 nm, and with an expected increase of the recording areal density of commercial recording disk media up to 10 Gbit/in$^2$ (1.6 Gbit/cm$^2$) within five years, the problem of the nanoscale defects within the thin film media will become increasingly significant.

With equipment like the optical microscope and the atomic force microscope (AFM), it is possible to observe and characterize certain surface defects. However, there is still very little development of methods to observe and characterize nanoscale in-depth defects such as voids and dislocations in magnetic thin film, particularly in a fast, easy and non-destructive way. Although the high resolution electron microscope (HRTEM) may be used to analyze the nanoscale structure in thin films and to detect the nanoscale defects in them, sample preparation is tedious and time consuming. Thus, the HRTEM has only limited application to defect detection in magnetic thin film devices manufactured on an industrial production line. Ferrofluid detection may only by used to localize and characterize micron size defects in magnetic thin films. Although, magnetic force microscopy may be used to localize and characterize submicron sized defects in magnetic thin films, the approximate location of each defect must be known beforehand. A media tester may be used together with surface observation equipment to localize submicron indepth defects in the magnetic recording film media. However, this requires a sample which includes a protection overcoat and lubricant layer. In addition, it is difficult to give meaningful information based on the average result over a big area in a short time.

An object of the invention as to provide a way of analyzing defects, especially nano-sized defects, in magnetic thin films which overcomes at least some of the limitations of existing techniques to enable various information about the defects to be gathered efficiently.

SUMMARY OF INVENTION

According to a first aspect of the present invention, there is provided a method of analyzing defects in a magnetic thin film, comprising: applying a magnetic field to the magnetic thin film; measuring the magnetizations of the magnetic thin film over a range of different field strengths; calculating a value representative of a magnetic hardness coefficient for the magnetic thin film from the magnetizations measured; comparing the calculated value with a reference value; and determining defect information in dependence upon the comparison made.

The present invention is particularly useful for analyzing nano-sized defects in magnetic thin films of nano-sized thickness because the magnetic hardness coefficient is very sensitive to defect variations. This is due to the fact that the defect size is comparable to the thickness of the magnetic thin film. The magnetic hardness coefficient may be calculated from certain magnetization readings which are substantially inversely proportional to the applied field. Usually, the magnetization becomes inversely proportional to the applied field as the magnetic thin film approaches saturation.

It is known that the magnetization of a ferromagnetic body when subjected to an ever increasing magnetic field H, tends to a limit. This high field behavior has been modeled by the Law of Approach to Saturation (LATS) as given by Becker and Doring [Ferromagnetismus, Julius Springer, Berlin, 1939, pages 154–167] which is expressed in the form of a series:

$$M = M_s(1 - a/H - b/H^2 -) + kH$$

where:

M is the magnetization of a body;

H is the applied field;

$M_s$ is the saturation magnetization;

a is the magnetic hardness coefficient b relates to the magnetocrystalline anistropy constant; and kH represents the forced magnetization.

The forced magnetization is the field induced increase in spontaneous magnetization, which is a very small contribution except at high field. Typically H has to be of the order of $10^5$ or $10^6$ Oe ($10^7$ or $10^8$ amperes per meter) before this last term becomes significant.

Néel [C. R. Acade. Sci., 220: 738(1945)] proved by experiment and theoretical analysis that the above equation may be used to characterise the saturation magnetization process for specimens with different densities made from iron powder. He found that the iron specimens become more difficult to magnetize as porosity increased, giving rise to larger magnetic hardness coefficients, a. Brown [Phys. Rev. Vol. 60:139(1941)] also showed that certain deformations, arising from dislocations of the lattice would give rise to an approach law varying as 1/H for the magnetization. The deformations result from the decrease (negative dislocation) or increase (positive dislocation) by one unit of the number of atoms which constitute successive rows of the crystal.

The present applicants have appreciated that the pioneering theoretical and experimental work carried out by Becker and Doring, Néel and Brown may be applied to the analysis of defects in magnetic thin film. The calculated value may correspond to $M_s a$ (that is the magnetic hardness coefficient multiplied by factor $M_s$) or it may in fact be the magnetic hardness coefficient. The type of defect information determined, in accordance with the present invention depends on the nature of the reference value.

The reference value may be representative of a magnetic hardness coefficient of a control specimen. The control specimen may be a comparable magnetic thin film having a predetermined defect level or concentration. Obviously, to give a meaningful result, the calculated value and reference value should be capable of comparison. For example, if the calculated value corresponds to $M_s a$, the reference value must correspond to $M_s a^1$, where $a^1$ represents the magnetic hardness coefficient of the control specimen.

Suppose it is necessary to ascertain the suitability of a magnetic thin film sample for a particular role. There may be a threshold defect level which, if exceeded, will suggest that the magnetic thin film sample is not suitable for the intended role. In which case, the reference value is determined by calculating the magnetic hardness coefficient for a control specimen of magnetic thin film having the threshold defect level. If the magnetic hardness coefficient for the sample is greater than that of the control specimen, the sample may be deemed unsuitable for the intended role.

Alternatively, the reference value may be representative of a magnetic hardness coefficient calculated for the magnetic thin film when the magnetic field is applied in a different direction. The magnetic field directions for the two magnetic hardness coefficient calculations are preferably non-parallel, and may be perpendicular. The present applicants have found that the magnetic hardness coefficient may vary with the direction in which the field is applied. The angular dependence of magnetic hardness coefficient provides a method for identifying certain defects in certain samples by evaluating the anistropy of the defects. For a simple case, two-dimension angle dependence (0–360 degree in film plane) is sufficient, for a complex case, three dimension angle dependence may be required.

To enhance defect information determination still further, the method may further comprise comparing the magnetic hardness coefficient and reference value with another reference value, the said another reference value being a magnetic hardness coefficient calculated for the magnetic thin film when the magnetic field is applied in another different direction. The magnetic field directions for calculating the magnetic hardness coefficient, the reference value and the said another reference value may be mutually orthogonal.

Suppose it is necessary to ascertain the predominant type of defect present in a single crystal sample. Lattice defects are classified by their geometry or shape. Point defects (e.g., a vacancy) are associated with only one lattice point; line defects (e.g., a dislocation lie along a line of lattice points); and surface defects (e.g., a grain boundary or a stacking fault) extend over at least two dimensions in the crystal. By evaluating the dependence of the magnetic hardness coefficient on the direction of applied field, it may be possible to determine the predominant type of defect present. For example, a magnetic hardness coefficient which is constant in three directions may indicate a preponderance of point defects, whereas a variation in magnetic hardness coefficient in all three directions may indicate the existence of a surface defect.

In another embodiment, the magnetization is measured for a selected part of the magnetic thin film. Accordingly, the value representative of the magnetic hardness coefficient calculated will be specific to the selected part. The reference value may be representative of the magnetic hardness coefficient calculated from magnetizations measured for a part other than the said selected part of the magnetic thin film. By recording the relative positions of the selected part and the said other part and repeating the measurement for yet other parts of the magnetic thin film, the variation in magnetic hardness coefficient across the magnetic thin film may be mapped.

According to a second aspect, there is provided a method for mapping defects in a magnetic thin film, comprising: applying a magnetic field to the magnetic thin film; measuring the magnetization at known positions of the magnetic thin film over a range of different field strengths; calculating a value representative of a magnetic hardness coefficient for each of the positions from the magnetizations measured; and plotting information corresponding to the relative positions and magnetic hardness coefficients calculated.

The mapping of magnetic hardness coefficient variation across a substrate is useful in production of magnetic thin film devices. By associating the higher coefficients with increased defect levels, it enables parts of the magnetic thin film liable to fail in use to be identified.

BRIEF DESCRIPTION OF THE DRAWINGS

Embodiments of the invention will now be described, by way of example, with reference to the accompanying drawings in which.

DETAILED DESCRIPTION OF DRAWINGS

Figure 1:
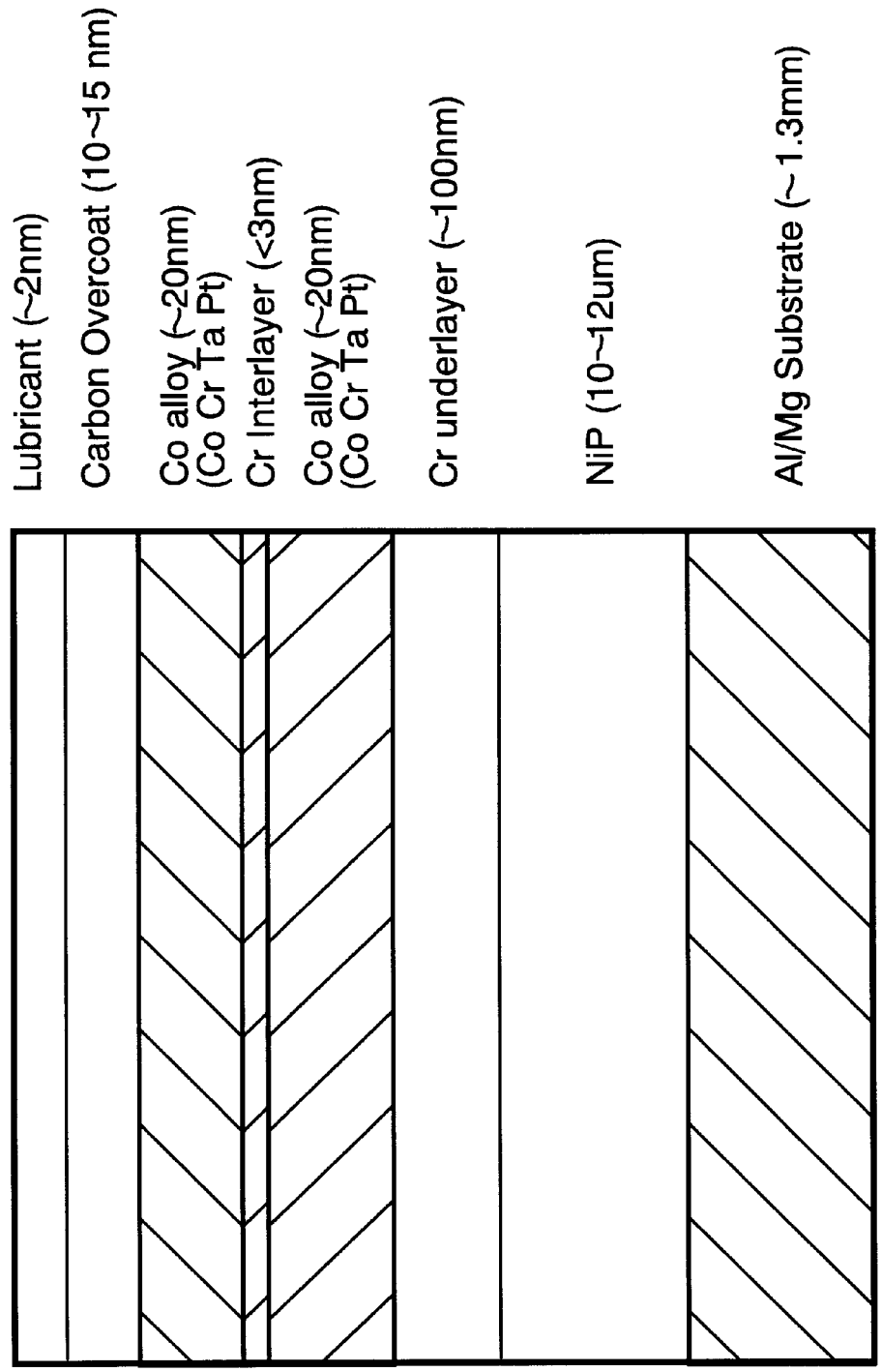
FIG. 1 is a cross-sectional view of a commercial magnetic thin film media (1997) which is used to illustrate methods embodying the present invention.

FIG. 1 illustrates the cross-section of a typical magnetic thin film media to which methods embodying the present invention are applicable. The typical thicknesses of the layers are as indicated. Such a media may be prepared for example by sputtering or electroplating a substrate.

A magnetic field is applied to a magnetic thin film sample and the resulting magnetizations of the sample were measured over a range of different field strengths. The magnetizations were measured using a Vibrating Sample Magnetometer produced by Digital Measurement System, Burlington, Mass. Other instruments for measuring magnetizations include a Magneto-Optical Kerr-Effect System, an Alternating Gradient Force Magnetometer, and a Superconducting Quantum Interference Device. The device used to measure magnetizations is not important, provided it is able to generate a field sufficient to saturate or substantially saturate the sample.

Figure 2:
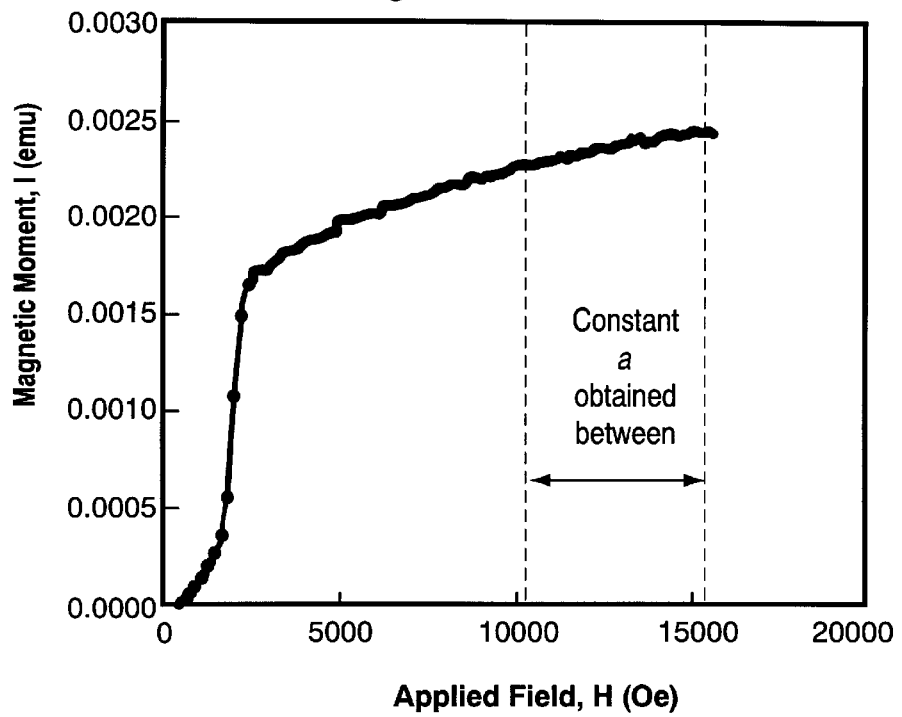
FIG. 2 illustrates a magnetization curve for the media of FIG. 1.

The magnetization is plotted against field strength to obtain a saturation magnetization curve as shown in FIG. 2. The saturation magnetization process may be considered as if divided into two parts. The first part which is at middle range of magnetic field (about 4 kOe–8 kOe or $3 \times 10^5$–$6 \times 10^5$ A/m is mainly controlled by kinds of magnetic anisotropies of the magnetic material and may be described by an inverse square law or $1/H^2$ term.

It is believed that the second part which is in high field range (about 10kOe–15 kOe or $8 \times 10^5$–$1.2 \times 10^6$ A/m; of the saturation magnetization process for the magnetic thin film media as shown in FIG. 2 may be well described by an inverse law or 1/H term in high field range (about 10kOe–15 kOe or $8 \times 10^5$–$1.2 \times 10^6$ A/m). From Néel's experiment on the iron powder and Brown's calculation about the influence of dislocations on the magnetization process, it is believed that the second part is mainly controlled by defects (including voids, dislocations and stack faultings etc) in the magnetic thin film samples.

Figure 3:
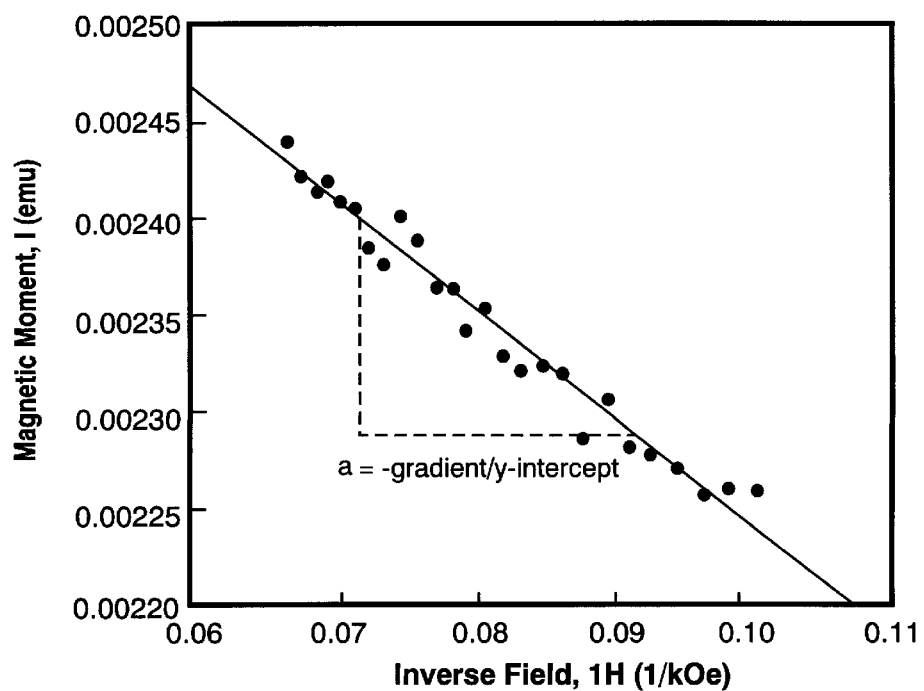
FIG. 3 illustrates the determination of magnetic hardness coefficient from the magnetization curve of FIG. 2.

If the magnetization is plotted against 1/H in high field range, the curve approximates to a straight line as shown in FIG. 3. The absolute value of the slope of the straight line is defined as the magnetic hardness coefficient a and it is believed that this relates to defects in magnetic thin films. Accordingly, the magnetic hardness coefficient is used to characterize the defects in magnetic thin film. It is of course to be appreciated that the range of the applied field used to determine the coefficient depends on the type of samples.

An experiment has been conducted in order to illustrate the above for magnetic thin films. As is known, there are many possible origins of defects in magnetic thin film media, such as poor plating NiP layer and insufficient cleaning of the substrate before sputtering and arcing and re-sputtering on a sample during sputtering. In this instance, a method of re-sputtering was chosen to induce on purpose more in-depth defects in magnetic recording thin film media because it is easy to control the degree of re-sputtering by applying various negative bias voltage to the substrate.

One set of 3.5 inch (8.9 cm) magnetic thin film media disks which had the structure as shown in FIG. 1 was prepared for this purpose, where CoCrTaPt layers within the disks were deposited at different negative bias voltages (0, 100, 200 and 300 V) while keeping the other deposition conditions constant. The magnetization curves for all the above-mentioned disks were obtained using the Vibrating Sample Magnetometer (VSM) which has a sensitivity of $10^{-5}$ emu for moment measurement. Samples with a 1 cm diameter were cut from the disks, and aligned so that the magnetic field was in the plane of the samples. The magnetization of the samples was measured along the tangential direction of the disks. The magnetic hardness coefficient (constant a) was calculated from the magnetization curves as described above.

Figure 4:
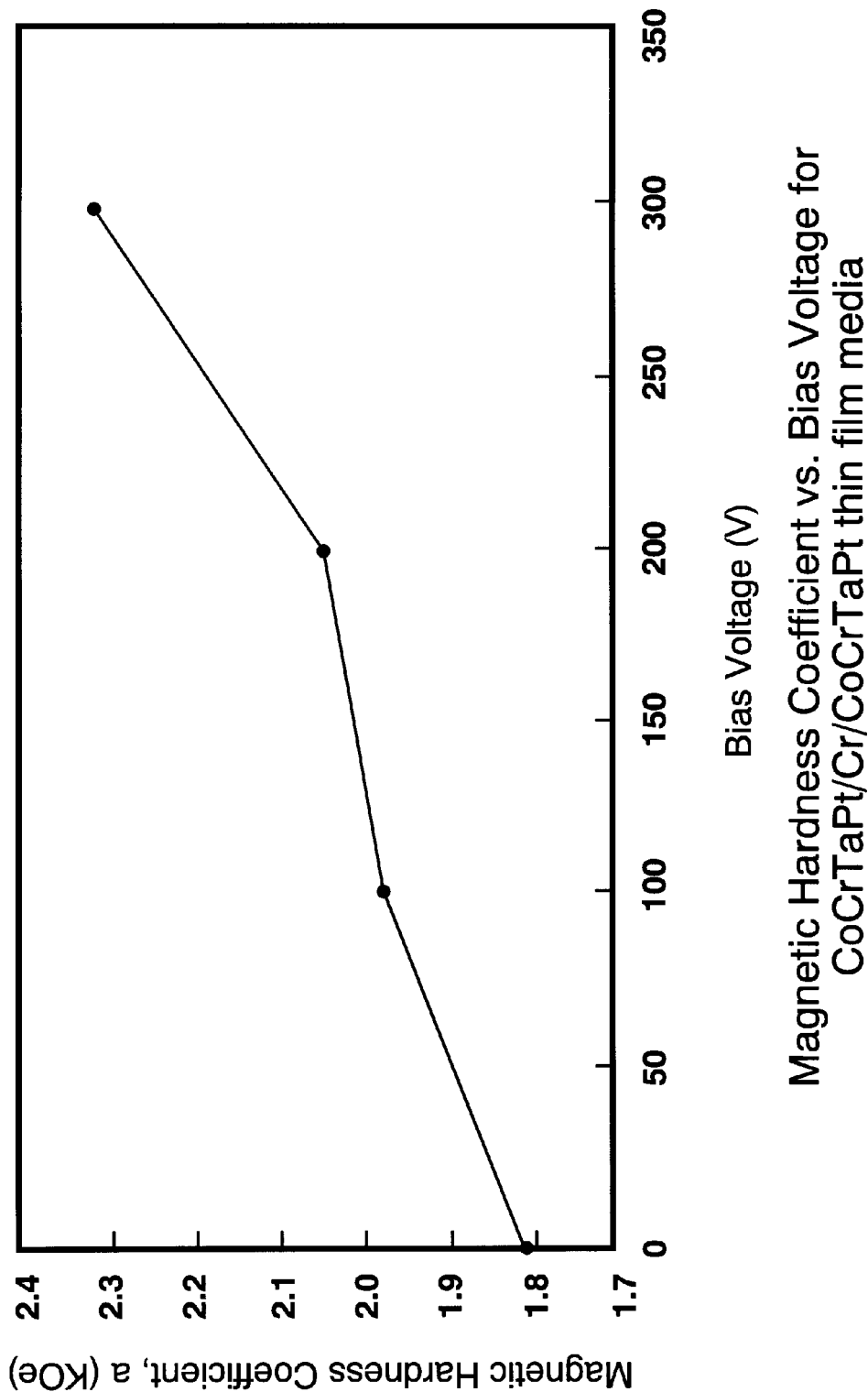
FIG. 4 illustrates the variation of magnetic hardness coefficient with negative bias voltage for sputtered CoCr-TaPt layers in the magnetic thin film media of FIG. 1.

FIG. 4 shows a graph of the magnetic hardness coefficient plotted against the bias voltage used to produce the samples. There is a 30% increase in the magnetic hardness coefficient when the bias voltage increases from 0 V to 300 V. It is known that the negative bias voltage induces re-sputtering in the growing thin film and that this will almost inevitably result in more defects such as dislocations and stack faultings in the film. Hence, FIG. 4 shows the relation of magnetic hardness coefficient with increasing levels of defects in the magnetic thin film media. The density of defects within the magnetic layer increases, thus resulting in a corresponding increase in the magnetic hardness coefficients.

Thus, by comparing the magnetic hardness coefficient of one sample with that of another (e.g., a control sample), it is possible to grade the samples according to the relative level of defects detected. For a magnetic thin film with mainly one kind of defect, the type of predominant defect may be determined by comparing magnetic hardness coefficients calculated when the magnetic field is applied in different (e.g., three mutually perpendicular) directions. As a simple example, suppose magnetic hardness coefficients are determined for various angles between the direction of applied magnetic field and a set reference direction in the plane of the magnetic thin film. From a graph of magnetic hardness coefficient verses angle, the predominant defect type in the sample may be identified. In addition, by using magneto-optical kerr-effect systems or other methods which measure magnetization in a non-destructive way at various positions over the magnetic thin film, calculation of the magnetic hardness coefficient would enable the location and distribution of defects in the magnetic thin film to be mapped.

What is claimed is:

1. A method of analyzing defects in a magnetic thin film, comprising:

applying a magnetic field to the magnetic thin film in a first direction;

measuring the magnetization of the magnetic thin film over a range of different field strengths;

calculating a value representative of a magnetic hardness coefficient for the magnetic think film from the magnetizations measured;

comparing the calculated value with a reference value; and determining defect information in dependence upon the comparison made.

2. A method according to claim 1, in which the reference value is obtained with the magnetic field applied in the first direction, and the reference value is representative of a magnetic hardness coefficient for a magnetic thin film control sample having a predetermined defect level.

3. A method according to claim 2, in which the calculated value and the reference value are determined when the magnetic field is applied in a different second direction.

4. A method according to claim 3, in which the first and second magnetic field directions are non-parallel.

5. A method according to claim 4, in which the first and second magnetic field directions are perpendicular.

6. A method according to claim 3, further comprising comparing the calculated values and reference values obtained with the magnetic field applied in the first and second directions, with another set of values comprising a calculated value and a reference value determined when the magnetic field is applied in a different third direction.

7. A method according to claim 6, in which the three different magnetic field directions applied to determine the calculated values and reference values are mutually orthogonal.

8. A method according to claim 1, in which the magnetizations are measured for a selected part of the magnetic thin film.

9. A method according to claim 8, in which the reference value is representative of a magnetic hardness coefficient calculated from magnetizations measured for a part other than the said selected part of the magnetic thin film.

10. A method according to claim 9, further comprising determining the relative positions of the selected part and the other part of the magnetic thin film, and plotting the relative positions with the respective values representative of magnetic hardness coefficients.

11. A method according to claim 10, further comprising:

calculating a value representative of a magnetization hardness coefficient for yet another part of the magnetic thin film, determining the position of the yet another part relative to the selected part of the other part, and plotting the same.

12. A method according to claim 1, in which the value representative of the magnetic hardness coefficient is determined in the range where the magnetization becomes substantially inversely proportional to the applied field.

13. A method according to claim 12, in which the value representative of the magnetic hardness coefficient is determined by calculating the rate of change of the magnetization with the inverse of the field applied.

14. A method of mapping defects in a magnetic thin film comprising:

applying a magnetic field to the magnetic thin film;

measuring the magnetization at positions of the magnetic thin film over a range of different field strengths;

calculating a value representative of a magnetic hardness coefficient for each of the positions from the magnetizations measured; and plotting the magnetic hardness coefficient distribution corresponding to the known positions of the magnetic thin film.

* * * * *